United States Patent [19]
Dane

[11] Patent Number: 5,490,975
[45] Date of Patent: Feb. 13, 1996

[54] STERILIZATION AND STORAGE CONTAINER TRAY

[75] Inventor: Gary T. Dane, Webster, N.H.

[73] Assignee: Poly-Vac Incorporated, Manchester, N.H.

[21] Appl. No.: 355,997

[22] Filed: Dec. 14, 1994

[51] Int. Cl.⁶ .................................................. A61L 2/00
[52] U.S. Cl. ...................... 422/300; 206/379; 206/438; 206/439
[58] Field of Search ..................... 422/300, 310, 422/104; 206/379, 438, 439, 443; 433/77; 211/69, 70

[56] References Cited

U.S. PATENT DOCUMENTS

| | | | |
|---|---|---|---|
| 4,643,303 | 2/1987 | Arp et al. | 206/370 |
| 4,728,504 | 3/1988 | Nichols | 422/297 |
| 4,783,321 | 11/1988 | Spence | 422/300 |
| 4,798,292 | 1/1989 | Hauze | 206/439 |
| 5,098,676 | 3/1992 | Brooks, Jr. | 422/292 |
| 5,172,810 | 12/1992 | Brewer | 422/300 |
| 5,215,726 | 6/1993 | Kudla et al. | 422/300 |
| 5,312,250 | 5/1994 | Ellman et al. | 206/379 |

Primary Examiner—Robert J. Warden
Assistant Examiner—Theresa T. Snider
Attorney, Agent, or Firm—Hayes, Soloway, Hennessey, Grossman & Hage

[57] ABSTRACT

A sterilization tray assembly for sterilizing, transporting and storing surgical instruments, having top and bottom mating enclosures. The mating enclosures each have a plurality of ports for permitting ingress and egress of gaseous sterilant. A rack is rotatably mounted within the enclosure, and has a plurality of spaced apertures into which surgical instruments may be removably inserted.

10 Claims, 4 Drawing Sheets

STERILIZATION AND STORAGE CONTAINER TRAY

FIELD OF THE INVENTION

This invention relates to sterile container systems generally, and more particularly to container systems for the sterilization and subsequent sterile storage of medical surgical instruments and the like.

BACKGROUND OF THE INVENTION

Surgical procedures are regularly performed using "sets" of pre-selected surgical instruments, each set being a collection of instruments established from experience to be useful in a given surgical procedure. For example, the surgical instruments expected to be used in an obstetrical procedure are grouped together to form a set and, as a set, are sterilized, stored on a pan or tray, and finally transported on that tray to the operating room when their use is required.

Sterilization of reusable and delicate, precision surgical instruments and their subsequent sterile storage is of paramount concern to surgeons and hospitals. Sterilized surgical instruments are essential during surgical procedures to minimize the risk of infection.

Some example prior art patents which provide for sterilization containers are Arp et al, U.S. Pat. No. 4,643,303; Nichols, U.S. Pat. No. 4,728,504, and Spence, U.S. Pat. No. 4,783,321. These prior art patents generally teach the use of baskets or trays to hold the instruments to be sterilized, and apertures in the baskets which allow for gross drainage of condensation from the baskets first to the container floor below the basket, and from the container floor to the outside.

U.S. Pat. No. 4,643,303 describes a sterilization container enclosing an instrument basket within a box-like base and cover. The container also includes clamps mounted to the container by hinges for releasably holding the cover to the base. U.S. Pat. No. 4,783,321 describes a sterilization container enclosing an instrument basket within a base and cover. The container also includes a latch mechanism for releasably holding the cover to the base.

Most of the prior art, for example, Nichols U.S. Pat. No. 4,728,504, provide for the placement of the instruments on a removable basket or tray which includes apertures formed on the bottom of the tray to allow for the drainage of condensation. The domed configuration of the tray bottom in U.S. Pat. No. 4,728,504 reportedly allows for sufficient surface area contact with the instruments such that condensate may be held between the instruments and the tray after sterilization. Such a risk of airborne bacterial contamination of remaining condensation after sterilization increases during increased storage of the sterilized instruments. Thus, it is imperative to remove as much condensation as possible from the container and from the instruments after sterilization.

Hauze, U.S. Pat. No. 4,798,292, describes a non-locking sterilization container with apertures arranged in rows and columns enclosing a flat surfaced insert with apertures arranged in rows and columns such that the apertures in the container and the insert are vertically aligned. Pegs are inserted in the insert apertures to provide horizontal separation of the instruments during sterilization and subsequent presentation of the instruments. The flat surface of the insert and the pegs increase the risk of condensation remaining in proximity to the instruments after sterilization.

The foregoing discussion of the prior art was taken largely from Brooks, U.S. Pat. 5,098,676 which describes an improved sterilization tray assembly for sterilizing, transporting and storing instruments, which overcomes the aforesaid and other disadvantages of the prior art. Brooks provides a sterilization tray assembly comprising an upper tray section including a plurality of upper tray ports spaced in a predetermined pattern; a lower tray section including a plurality of lower tray ports spaced in a predetermined pattern; and locking means for engaging the upper tray section and the lower tray section to form a sealing contact between the upper and lower tray sections. A mat made of silicone rubber and sized to fit the tray is positioned between the tray sections. The mat has an upper surface and a lower surface, and includes a plurality of ports in the mat spaced in a predetermined pattern wherein the mat ports and the lower tray ports are in vertical alignment. The mat also has a plurality of upwardly tapered, vertical projections spaced in a predetermined pattern on the upper surface, the vertical projections having tips at their free ends to provide support for instruments above the upper surfacer and a plurality of downwardly projecting support feet depending from the lower surface spaced in a predetermined pattern for spacing the lower surface above the lower tray section.

The sterilization tray assembly as described in Brooks U.S. Pat. No. 5,098,676 is available commercially from PolyVac, Inc. of Manchester, N.H., and has achieved substantial commercial success. However, while the silicone rubber mat as described in U.S. Pat. No. 5,098,676 provides a convenient support for larger surgical instruments; smaller instruments may not be securely held. Accordingly, Poly-Vac, Inc. and others have introduced sterilization trays including one or more holding strips specifically designed to releasably hold selected surgical instruments.

The present invention is an improvement over the sterilization, transporting and storage container trays such as described in U.S. Pat. No. 5,098,676.

SUMMARY OF THE INVENTION

In one aspect, the present invention provides a sterilization, transporting and storage container tray assembly for a surgical instrument kit. The tray assembly includes top and bottom locking trays enclosing a rack assembly rotatably mounted in the bottom tray or in an instrument tray loaded in the bottom tray. The rack includes a plurality of spaced apertures for accommodating selected surgical instruments, pins, screws or the like. The apertures have inner diameters selected for accommodating the selected instruments, etc. so that the instruments readily may be loaded into the rack for sterilization, and readily may be removed by the surgeon during an operation. The rack is rotatably mounted in the bottom tray or in an instrument tray loaded in the bottom tray so that the rack may be rotated to a horizontal position to reduce the possibility that the instruments mounted therein might be dislodged during transport. The rack rotatable mounting also permits the user to orient the rack at an angle which facilitates both the identification and removal of the small instruments. In a preferred embodiment of the invention, the rotatable rack comprises a two-piece assembly including a core member having a plurality of spaced apertures, and a cover member having a plurality apertures which overlap the apertures in the core member, at least in part.

Ports are provided in the top and bottom trays for permitting ingress and egress of steam or other gaseous sterilants. The optional instrument tray also may have one or more ports for permitting free flow of steam or other gaseous sterilants within the tray assembly, and condensation drainage, and preferably is separated from the interior walls of the bottom tray by spacers or projections so as to permit additional free flow of steam and other gaseous sterilant within the tray assembly, and further facilitate condensation drainage.

Completing the sterilization, transporting and storage tray assembly are at least one pair of locking hinges or clips for locking the top and bottom trays together. The locking hinges or clips may comprise spring metal clips for example, as shown in FIG. 8 of the aforesaid U.S. Pat. No. 5,098,676 to Brooks.

BRIEF DESCRIPTION OF THE DRAWINGS

The foregoing and other objects of the present invention and various features and details of the operation and construction thereof are hereinafter more fully set forth with reference to the accompanying drawings, wherein like numerals depict like parts, and wherein.

DETAILED DESCRIPTION OF THE PREFERRED EMBODIMENT

Figure 1:
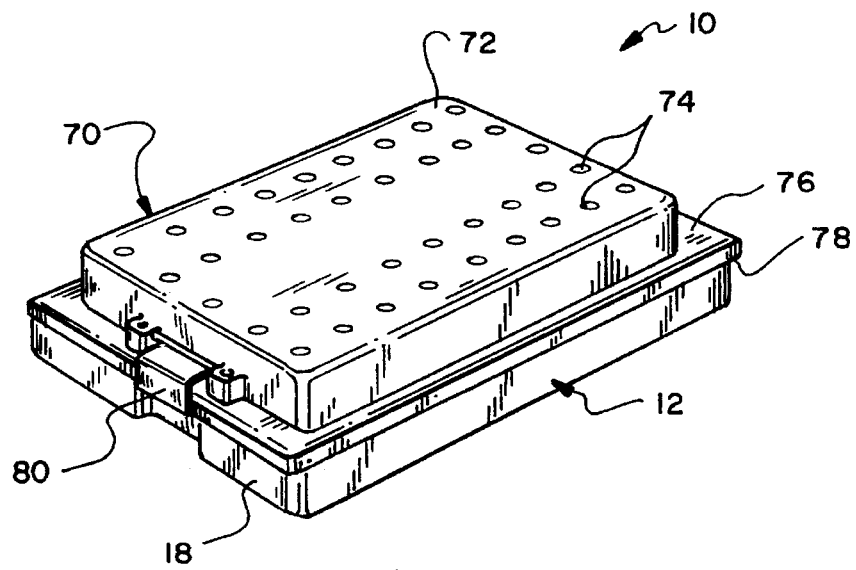
FIG. 1 is a perspective view of the preferred embodiment of the invention showing the tray assembly in the closed and locked position.
Figure 2:
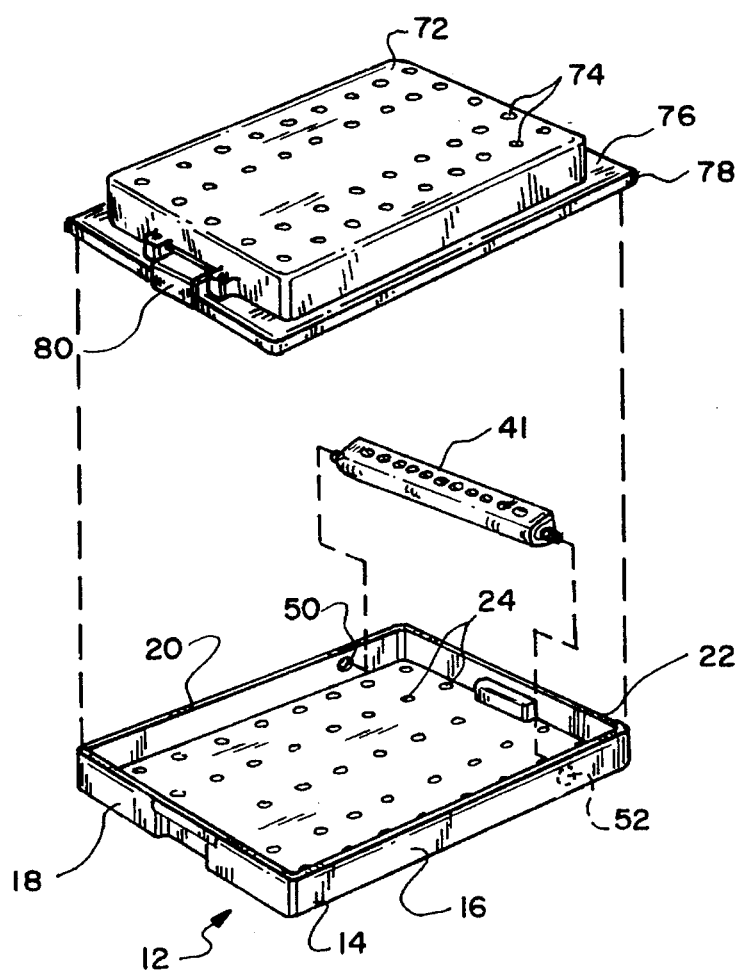
FIG. 2 is a partially exploded view of FIG. 1.
Figure 3:
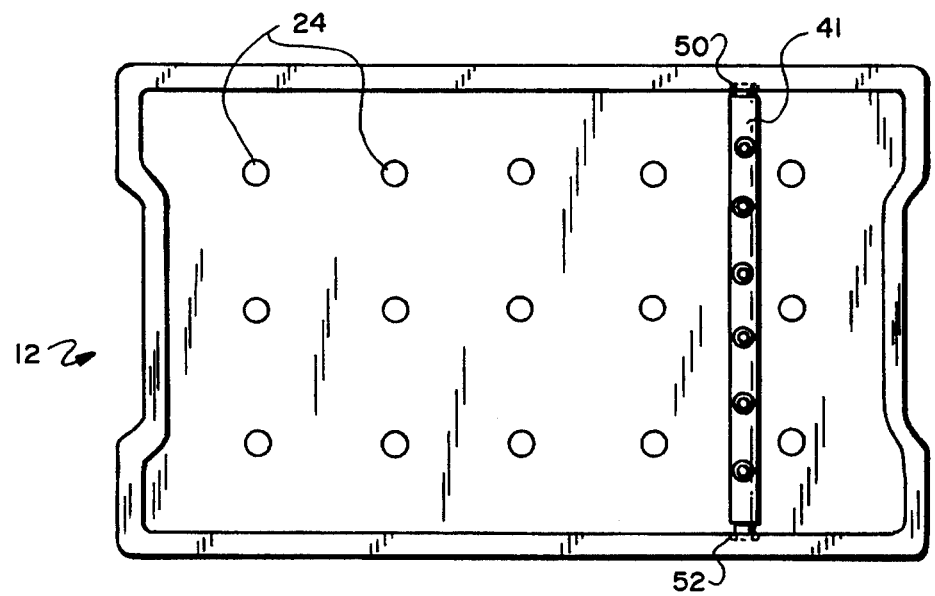
FIG. 3 is an overhead plan view of the tray assembly of FIG. 3, with the top tray removed.
Figure 4:
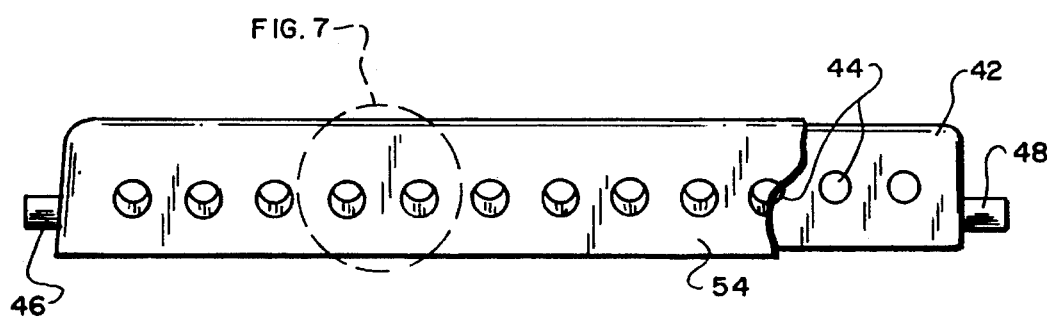
FIG. 4 is a partial sectional view similar to FIG. 3, and showing details of the rotatably mounted rack of the present invention.

Referring now to the drawings, and in particular to FIGS. 1–3, the sterilization, transporting and storage tray assembly of the present invention is indicated generally by numeral 10. The tray assembly 10 consists of a box-like bottom tray 12 having a bottom 14 and four generally perpendicular upwardly projecting continuous sidewalls comprising a front sidewall 16, a left sidewall 18, a back sidewall 20 and a right sidewall 22. Tray bottom 14 includes a plurality of spaced apertures 24 arranged in a predetermined pattern. Apertures 24 permit ingress and egress of steam or other gaseous sterilants, and allow for condensation drainage.

A feature and advantage of the present invention is to provide a surgical instrument delivery system for pre-defined surgical procedures in which a selection of tools with a range of sizes and styles may be prepackaged for use in a logical sequence of operations. However, certain tools such as pins, screws, burrs, and the like employed in certain surgical procedures such as dental implant surgery, facial bone reconstruction surgery and the like, may be quite small. The present invention provides a rotatably mounted rack 41 for holding such small tools.

Referring in particular to FIGS. 4–7, the rotatable rack 41 made in accordance with the present invention comprises an elongate, preferably solid bar 42 rotatably mounted, about its long axis on tray 12. Bar 42 is formed of a rigid, heat and moisture resistant material such as polypropylene or other material suitable for use in sterilization, and includes integrally formed bottom end pins 46, 48, which are press mounted in receiving holes 50, 52 in tray walls 16, 20. A plurality of spaced holes 44 are drilled in bar 42 for accommodating specific tools as will be described in detail below.

Figure 5:
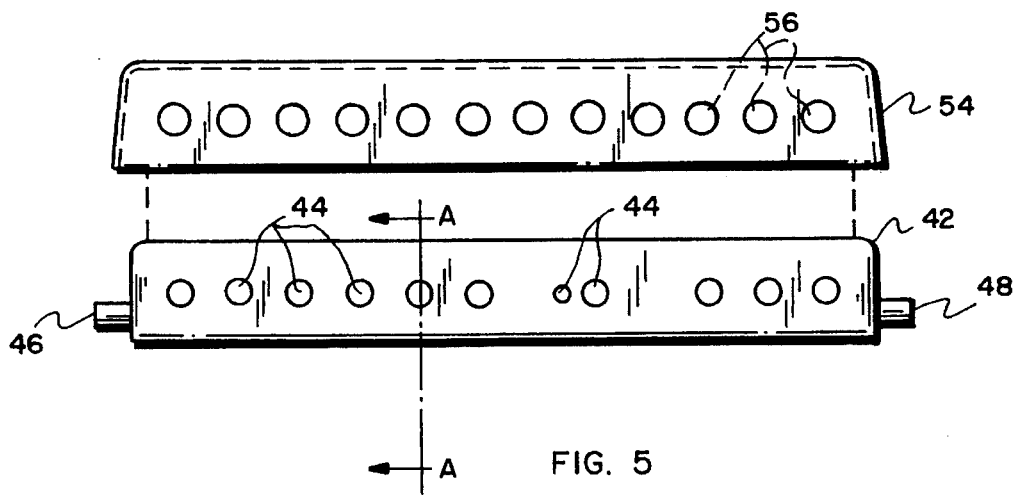
FIG. 5 is an exploded top plan view showing details of a two-piece rotatable rack assembly in accordance with a preferred embodiment of the invention.
Figure 6:
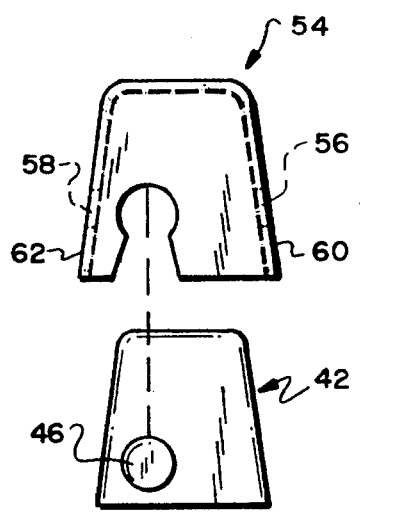
FIG. 6 is an end view showing details of the two piece rotatable rack of FIG. 5.
Figure 5A:
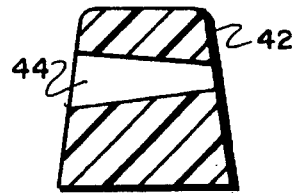
FIG. 5A is a partial sectional view taken along the line A in FIG. 5.
Figure 7:
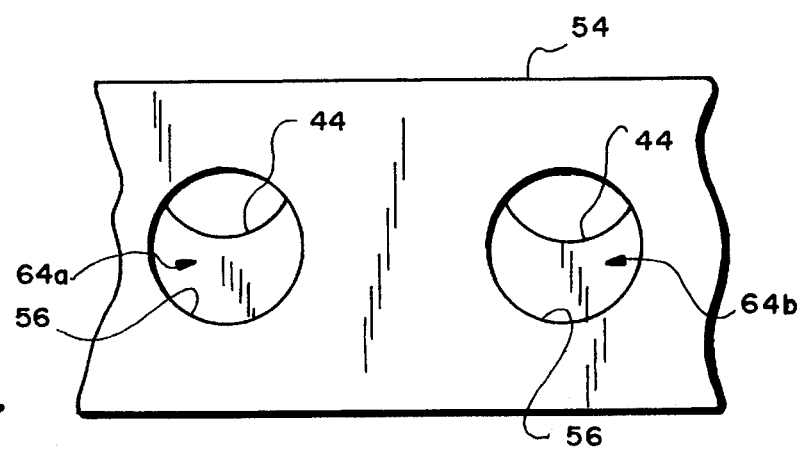
FIG. 7 is an enlarged top plan view of the portion designated "FIG. 7" in FIG. 4.

A three-sided cover 54 formed of a heat and moisture resistant, resiliently-flexible material such as a thermoplastic or other resiliently flexible material suitable for sterilization, is snap-fitted over bar 42. Holes 56 and 58 are provided through walls 60 and 62, respectively, of cover 54, and are located so as to overlap in part holes 44 in bar 42 when cover 54 is in place thereon, whereby to define arcuate shaped holes 64A, 64B . . . for releasably gripping the shanks of small tools such as drill bits, pins and the like. In order to accommodate different sized tools, holes 44 may be varied in dimension and position relative to holes 56 (FIG. 5). Preferably holes 44 are drilled completely through bar 42 so as to permit drainage, i.e. through holes 58 in cover wall 62. Also, in accordance with a preferred embodiment of the invention, holes 44 are tapered (see FIG. 5A) so as effectively to limit the depth a tool may be loaded into rotatably rack 41 which in turn facilitates removal of the tool by the surgeon. On the other hand, the misalignment of holes 56 relative to holes 44 produces a resiliently deformable gripping structure which can accommodate the different rates of thermal expansion, for example, between the tools which are typically formed of stainless steel or a ceramic, and the rack 41. Forming rack 41 in two pieces as above described also facilitates custom manufacturing of the rack to accommodate different sized tools since it is only necessary to change the size and location of the holes in bar 42. Also, providing holes 58 in wall 62 permits the flow of steam or other gaseous sterilants to the base of the tools, and also facilitates the drainage of condensation.

Top 70 is of a box-like shape and includes a top surface 72 having a plurality of spaced apertures 74 arranged around the periphery of the top surface 72 to permit the ingress and egress of steam or other gaseous sterilants during sterilization, and drainage of condensation from the top surface 72. Top 70 includes an outwardly projecting peripheral ridge section 76, and a downwardly projecting lip section 78 which together engage the top portions of walls 16, 18, 20 and 22 of base 12 when the top 70 is locked upon the base 12. This sealing contact causes the steam of other gaseous sterilants to ingress and egress the container tray 10 only through apertures 24 and 74.

Completing the sterilization and storage container tray of the present invention are C-shaped locking hinges 80 made of a flexible metal or plastic which are attached to top 70 by hinge pins (not shown) at the midpoint position of the opposite ends of top 70 as shown in FIGS. 1–3. The locking hinges 80 pivot about hinge pins between a locking and non-locking position as described in U.S. Pat. No. 5,098,676 to Brooks.

While particular embodiments of the present invention have been illustrated and described herein, it is not intended to limit the invention, and changes and modifications may be made thereon within the scope of the following claims. For example, when rack 41 is rotatably mounted directly in the bottom tray, the bottom tray may serve both as the enclosure and instrument tray. In such case, the tray bottom should include integrally formed stand-offs or feet for raising the bottom to allow for condensation drainage. Alternatively, a mat having a plurality of tapered support fingers and feet may be provided in the bottom tray, e.g. as described in U.S. Pat. No 5,098,676 to Brooks, for accommodating larger sized tools.

Figure 8:
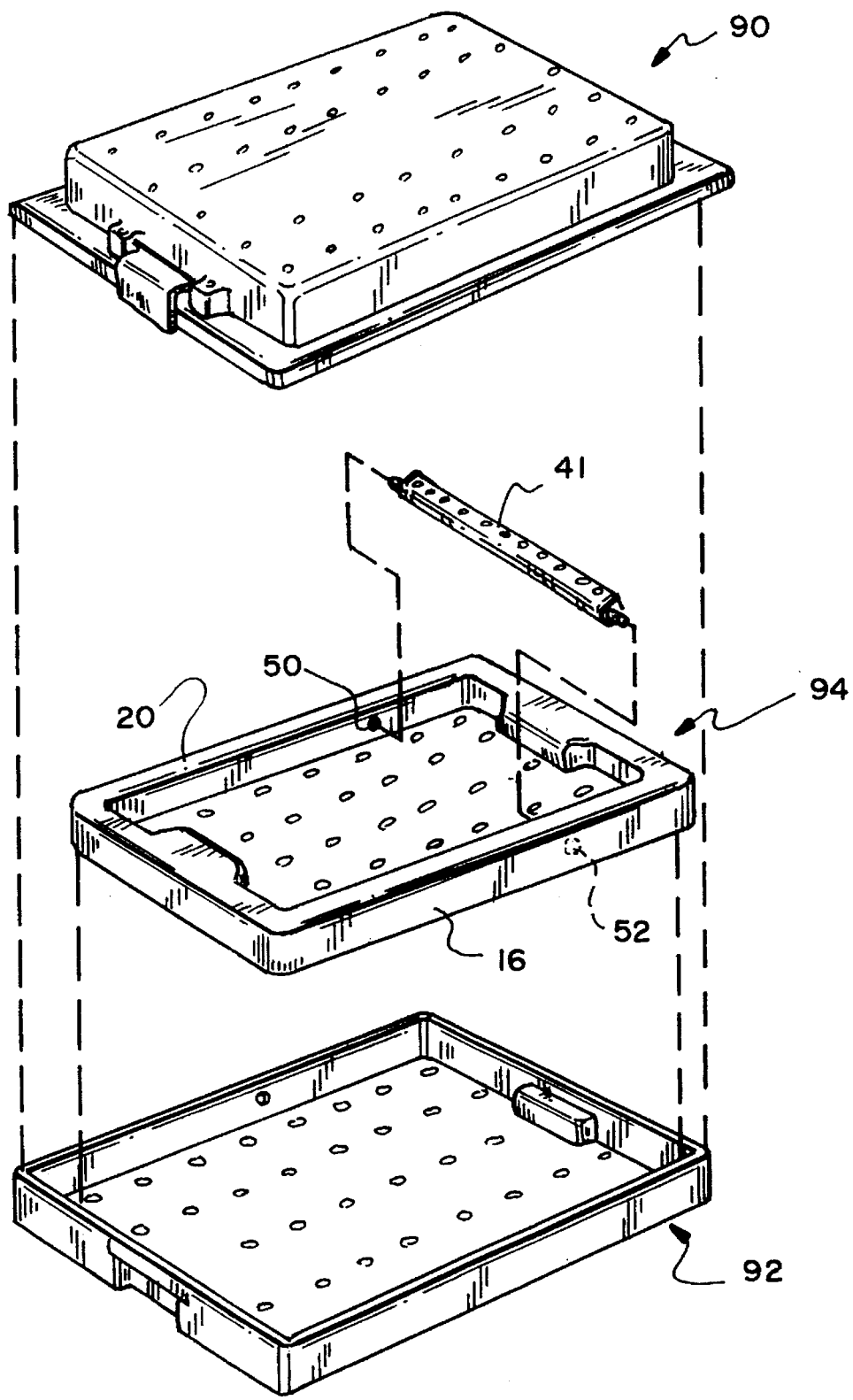
FIG. 8 is a view similar to FIG. 2, and showing yet another embodiment of the present invention.

Alternatively, as shown in FIG. 8, the sterilization tray assembly may comprise top and bottom mating enclosures 90,92, and including an instrument rack 94 fitted within the enclosure. As before, the top 90, bottom 92 and also the instrument rack 94 should have a plurality of apertures for permitting ingress and egress of steam or other gaseous sterilants, and allow for condensation drainage. The rotatable rack 41 made in accordance with the present invention may be mounted on instrument rack 94.

Still other changes may be made without departing from the scope of the invention.

What is claimed is:

1. In a sterilization tray assembly for sterilizing, transporting and storing surgical instruments comprising top and bottom mating enclosures, said mating enclosures each including a plurality of ports for permitting ingress and egress of gaseous sterilant; and means for locking said mating enclosures to one another, the improvement which comprises a rack rotatably mounted within the bottom enclosure, said rack having a plurality of spaced apertures into which surgical instruments may be removably inserted, said rotatable rack comprising an aperatured core member and including an aperatured resilient, flexible cover member surrounding said core member at least in part.

2. In a tray assembly according to claim 1, wherein the apertures in said core member and the apertures in said cover member overlap each other, in part.

3. In a tray assembly according to claim 1, wherein said cover member has three walls and apertures are provided in opposite walls of said cover member.

4. In a tray assembly according to claim 1, wherein the apertures in said core member are tapered.

5. In a sterilization tray assembly for sterilizing, transporting and storing instruments, and comprising top and bottom mating trays, an instrument tray fitted within the bottom tray, and means for locking said mating trays to one another, the improvement which comprises a rack rotatably mounted on said instrument tray, said rack having a plurality of spaced apertures into which surgical instruments may be removably inserted, said rack comprising an aperatured core member and including an aperatured resilient, flexible cover member surrounding said core member at least in part.

6. In a tray assembly according to claim 5, wherein said apertures in said core member vary in size.

7. In a tray assembly according to claim 5, wherein the apertures in said core member and the apertures in said cover member overlap each other, in part.

8. In a tray assembly according to claim 5, wherein the cover member has two walls and apertures are provided in opposite walls of said cover member.

9. In a tray assembly according to claim 5, wherein the apertures in said core member are tapered.

10. In a tray assembly according to claim 5, wherein said rack is rotatably mounted to the instrument tray on end pins carried by the rack.

* * * * *

UNITED STATES PATENT AND TRADEMARK OFFICE
CERTIFICATE OF CORRECTION

PATENT NO. : 5,490,975
DATED : February 13, 1996
INVENTOR(S) : Gary T. DANE

It is certified that error appears in the above-indentified patent and that said Letters Patent is hereby corrected as shown below:

Claim 8, Col. 6, line 25, "two" should be --three--.

Signed and Sealed this

Twenty-fifth Day of June, 1996

Attest:

BRUCE LEHMAN

Attesting Officer

Commissioner of Patents and Trademarks